United States Patent [19]
Tai et al.

[11] Patent Number: 5,214,144
[45] Date of Patent: May 25, 1993

[54] PROCESS FOR THE PREPARATION OF 4-HALOQUINAZOLINES

[75] Inventors: Jimmy J. Tai; James W. Ringer; Karl L. Krumel; Richard C. Krauss, all of Midland, Mich.

[73] Assignee: DowElanco, Indianapolis, Ind.

[21] Appl. No.: 772,523

[22] Filed: Oct. 7, 1991

[51] Int. Cl.$^5$ ............................................. C07D 239/72
[52] U.S. Cl. ..................................... 544/283; 544/286
[58] Field of Search ............... 544/283, 286, 334, 283, 544/286

[56] References Cited

U.S. PATENT DOCUMENTS 1,880,447 10/1932 Hentrich et al. ..................... 544/283
3,505,331 4/1970 Hitchings et al. ................... 544/250
4,672,116 6/1987 Bandurco et al. ................... 544/286

FOREIGN PATENT DOCUMENTS 326329 8/1989 European Pat. Off. .

OTHER PUBLICATIONS

Anderson et al., Synthesis, 1976, 398–399.
Botta et al., Journal of Heterocyclic Chemistry, 26 (1989) 883–4.
Brown, The Pyrimidines, Supplement I, pp. 116–117, R3 (1970).
Fieser & Fieser pp. 284–289 (1967).
Amarego J. Appl. Chem. 11 pp. 70–72, (1961).

*Primary Examiner*—Mukund J. Shah
*Assistant Examiner*—Matthew V. Grumbling
*Attorney, Agent, or Firm*—Craig E. Mixan; Kenneth L. Loertscher

[57] ABSTRACT

4-Haloquinazolines can be prepared by the halogenation of the corresponding 4-hydroxyquinazolines with a phosphoryl, thionyl or carbonyl halide in the presence of a catalytically effective amount of a N,N-dialkylformamide. The reaction is catalyzed by the addition of soluble organic halide salts.

10 Claims, No Drawings

PROCESS FOR THE PREPARATION OF 4-HALOQUINAZOLINES

FIELD OF THE INVENTION

The present invention concerns a process for the preparation of 4-haloquinazolines by the halogenation of the corresponding 4-hydroxyquinazolines. More particularly, the present invention concerns the accelerated halogenation of 4-hydroxyquinazolines by Vilsmeier reagent in the presence of a catalytic amount of a soluble halide salt.

BACKGROUND OF THE INVENTION

Substituted quinazolines (I),

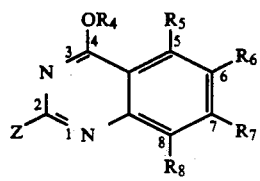

such as those described in EP 326,329, are valuable as plant fungicides, miticides and insecticides. Compounds of this family have generally been prepared by the reaction between a 4-haloquinazoline and an alcohol. The 4-haloquinazolines in turn are prepared by the halogenation of the corresponding 4-hydroxyquinazolines.

The recommended procedure for converting a 4-hydroxyquinazoline to the corresponding 4-haloquinazoline calls for the use of a relatively unstable triphenylphosphite-halogen complex as the preferred halogenating agent. This procedure requires at least one equivalent of triphenylphosphite-halogen reagent, the use of an additional equivalent of a tertiary amine base, an inert organic solvent and operation at less than about −15° C. In addition, the process is relatively complex, involving numerous recovery and recycle operations. A simplified process that eliminates some of the drawbacks associated with the use of triphenylphosphite-halogen as the halogenating agent is highly desirable.

SUMMARY OF THE INVENTION

We have now found that the desired halogenation can be accomplished by the use of Vilsmeier reagent. Furthermore, the reaction can be substantially accelerated by the addition of a catalytic amount of certain forms of halides. Therefore, the present invention concerns a process for the preparation of 4-haloquinazolines of formula (II)

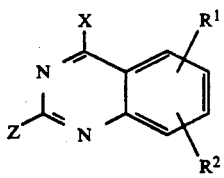

wherein
X represents Cl or Br,
Z represents H, Cl, CH$_3$ or OCH$_3$,
R$^1$ and R$^2$ are independently H, F, Cl, Br, R, OR, SR or NO$_2$, and R represents a straight or branched, saturated alkyl group of from 1 to 4 carbon atoms optionally substituted with F or Cl,
which comprises contacting a 4-hydroxyquinazoline of formula (III)

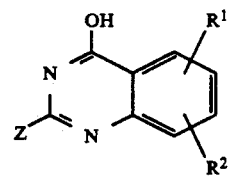

wherein
Z, R$^1$, R$^2$, and R are as previously defined,
with a carbonyl, thionyl or phosphoryl halide in the presence of a catalytic amount of a N,N-dialkylformamide and in the presence of a catalytic amount of a soluble halide salt.

The process of the present invention advantageously eliminates the need for a relatively unstable halogenating agent, the need of an organic solvent and the need of an equivalent of a tertiary amine base. In addition, unit operations are substantially simplified and the reaction need no longer be run with refrigeration.

DETAILED DESCRIPTION OF THE INVENTION

As used herein, the terms "alkyl" and "lower alkyl" are meant to designate straight or branched, saturated alkyl groups of from 1 to 4 carbon atoms.

Where individual members of the halogen family are not specifically listed, the general terms "halogen", "halide", "halo" and "hal", as used herein, are meant to be construed as being limited to chloro and bromo.

The 4-hydroxyquinazoline starting materials are known compounds and may be prepared as described in EP 326,329 and the references cited therein. Preferred starting materials are those in which Z represents H and in which R$^1$ and R$^2$ independently represent H, F, Cl, R or OR. The most preferred starting materials are those in which Z and R$^2$ represent H and in which R$^1$ represents H, F, CH$_3$ or OCH$_3$. R$^1$ is preferably located in the 5-, 6- or 8-position of the quinazoline ring system.

Vilsmeier reagent is generally considered to be a 1:1 complex of dimethylformamide and phosphoryl halide, thionyl halide or carbonyl halide; see, for example, Fieser and Fieser in "Reagents for Organic Synthesis", vol. 1, John Wiley & Sons, (1967) pp 284–5 and 286–9. Although this reagent can be prepared using an N-formyl derivative of any secondary amine, N,N-dialkylformamides are preferred and dimethylformamide is most preferred. While either a phosphoryl halide, a thionyl halide or a carbonyl halide can be used to prepare the reagent, the thionyl halide is preferred in terms of convenience and safety, and in so far as the by products, sulfur dioxide and hydrogen halide, are more easily handled. The chloride is preferred to the bromide.

It is often convenient to use the phosphoryl, thionyl or carbonyl halide as the reaction solvent in lieu of a more typical organic solvent. Although the Vilsmeier reagent is generally used in stoichiometric amounts relative to the 4-hydroxyquinazoline, when the phosphoryl, thionyl or carbonyl halide is used in large excess as the solvent, e.g., from about 5 to about 100 equivalents of phosphoryl, thionyl or carbonyl halide per equivalent of the 4-hydroxyquinazoline, only a catalytic amount of the N-formyl derivative of a secondary amine is required. Once it is spent in the halogenation reaction, the actual reagent is rapidly replenished by forming a new complex with the solvent. Although the reaction rate is dependent on the concentration of the N-formyl derivative of a secondary amine, the use of only from about 0.01 to about 0.15 equivalents of dialkylformamide per equivalent of the 4-hydroxyquinazoline is preferred.

With the use of only 0.01 to 0.15 equivalents of dialkylformamide per equivalent of the 4-hydroxyquinazoline, the conversion may not proceed as rapidly as desired. The reaction, however, can be accelerated by the addition of a catalytically effective amount of a soluble halide salt. Soluble halide salts are generally those containing organic cations and include, but are not limited to, aromatic amine hydrohalides, quaternary ammonium or phosphonium halides and tertiary ammonium halides. By an aromatic amine hydrohalide is meant the hydrohalide salt of an aromatic N-heterocycle, such as, for example, pyridinium hydrochloride or the isomeric picolinium hydrochlorides. By quaternary ammonium or phosphonium halide is meant the tetraalkyl or aryl ammonium or phosphonium halides, such as, for example, tetramethylammonium chloride, tetraphenylphosphonium chloride, benzyltriethylammonium bromide, nonyltriphenylphosphonium chloride and tetrabutylammonium bromide. By tertiary ammonium halide is meant the hydrohalide salt of a tertiary amine, such as, for example, the hydrochloride salt of triethylamine. The chlorides are generally preferred over the bromides. The soluble halide salt is generally employed in an amount from about 0.05 to about 1.0 equivalents per equivalent of the 4-hydroxyquinazoline.

The process is usually conducted by placing the 4-hydroxyquinazoline, the phosphoryl, thionyl or carbonyl halide and a soluble halide salt in a vessel and then adding a catalytic amount of the N,N-dialkylformamide. The mixture is allowed to react, typically at reflux, until the halogenation is complete. Since 4-haloquinazolines are typically unstable, have an irritating odor and are suspected mutagens, it is undesirable to isolate them as such. Therefore, the 4-haloquinazolines are usually reacted in situ with an alcohol prior to isolation or analysis. Excess phosphoryl, thionyl or carbonyl halide is first evaporated; addition of alcohol then consumes any residual phosphoryl, thionyl or carbonyl halide and converts the 4-haloquinazoline to the corresponding alkoxy analog. The resulting 4-alkoxy derivatives can be isolated by standard techniques.

Temperature is not critical; the reaction typically takes place at temperatures between 50 and 105° C. and is most conveniently carried out at the reflux temperature of the mixture. Operating pressures are not critical and may vary from atmospheric pressure to superatmospheric. While superatmospheric pressures may be appropriate when using a carbonyl halide, atmospheric pressure is satisfactory and is preferred for phosphoryl halides or thionyl halides.

The following examples are presented to illustrate the invention and should not be construed as limiting the scope of the invention. The 4-haloquinazolines are reacted in situ with an alcohol under acidic conditions prior to isolation or analysis.

EXAMPLE 1

Preparation of 4-Chloroquinazoline

A series of chlorination experiments was conducted according to the following procedure. The results of these experiments are summarized in Table I.

4-Hydroxyquinazoline (21.9 grams (g), 0.15 mole), thionyl chloride (150 milliliters (mL), 244 g, 2.06 mole) and a specified amount of catalyst, if any, were introduced into a reaction flask and a specified amount of dimethylformamide (DMF) was added. The mixture was refluxed (75°-78° C.) until the reaction was complete as determined by a clearing of the solution and by gas chromatographic analysis of the reaction mixture. Reaction samples were quenched in n-butanol to destroy excess thionyl chloride and to convert the unstable 4-chloroquinazoline into the 4-butoxy analog.

TABLE I

Summary of Preparations of 4-Chloroquinazolines

| Catalyst | mole[1] catalyst | mole[1] DMF | Time[2] hr |
|---|---|---|---|
| — | — | 0.100 | 1.5 |
| — | — | 0.030 | 8–10 |
| — | — | 0.020 | >24 |
| pyr[3] | 1.0 | 0.030 | 2.0 |
| TMAC[4] | 0.4 | 0.018 | 1.5 |
| TMAC[4] | 0 09 | 0.017 | 3.0 |
| TMAC[4] | 0.1 | 0.010 | 6.5 |

[1] mole equivalents with respect to 4-hydroxyquinazoline
[2] time to completion (hours)
[3] pyridinium hydrochloride
[4] tetramethylammonium chloride

EXAMPLE 2

Preparation of 4-Chloroquinazoline and Conversion to 4-[2-[4-(t-butyl)phenyl]ethoxy]-quinazoline 4-Hydroxyquinazoline (21.9 grams (g), 0.15 mole), thionyl chloride (150 milliliters (mL), 244 g, 2.06 mole) and tetramethylammonium chloride (TMAC, 16.4 g, 0.15 mole) were introduced into a reaction flask and dimethylformamide (0.202 g) was added. The mixture was refluxed for 1.5 hours (hr), at which point the reaction mixture turned clear. The thionyl chloride was evaporated and chlorobenzene was added as a solvent and as a chaser to remove any residual thionyl chloride. 4-(t-Butyl)phenylethanol (28.1 g) was added to the chlorobenzene solution and anhydrous hydrochloric acid was briefly sparged into the reaction mixture which was heated to 35°-40° C. After cooling, the solution was washed with 300 mL of 1.0 percent aqueous ammonia and the solvent was evaporated under reduced pressure to provide a solid residue. The product was recrystallized from hexane to give crystals melting at 70°-71° C.

What is claimed is:

1. A process for the preparation of 4-haloquinazolines of formula (II)

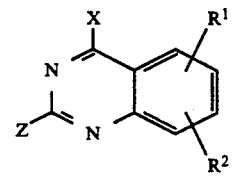

wherein

X represents Cl or Br,

Z represents H, Cl, CH$_3$ or OCH$_3$,

R$^1$ and R$^2$ are independently H, F, Cl, Br, R, OR, SR or NO$_2$, and

R represents a straight or branched, saturated alkyl group of from 1 to 4 carbon atoms optionally substituted with F or Cl, which comprises contacting a 4-hydroxyquinazoline of formula (III)

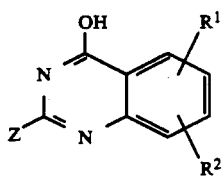

wherein

Z, R$^1$, R$^2$, and R are as previously defined, with a carbonyl, thionyl or phosphoryl halide in the presence of a catalytic amount of a N,N-dialkylformamide and in the presence of a catalytic amount of a soluble halide salt.

2. The process of claim 1 in which Z and R$^2$ represent H and in which R$^1$ represents H, F, CH$_3$ or OCH$_3$.

3. The process of claim 2 in which R$^1$ is located in the 5-, 6- or 8-position of the quinazoline ring system.

4. The process of claim 1 in which the N,N-dialkylformamide is dimethylformamide.

5. The process of claim 1 in which X represents Cl and the carbonyl, thionyl or phosphoryl halide is thionyl chloride.

6. The process of claim 1 in which the soluble halide salt is a tetraalkylammonium chloride.

7. A process for the preparation of 4-chloroquinazolines of formula (IIa)

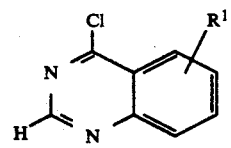

wherein

R$^1$ represents H, F, Cl, R, or OR, and

R represents a straight or branched, saturated alkyl group of from 1 to 4 carbon atoms optionally substituted with F or Cl, which comprises contacting a 4-hydroxyquinazoline of formula (IIIa)

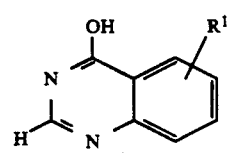

wherein

R$^1$ and R are as previously defined, with thionyl chloride in the presence of a catalytic amount of a N,N-dialkylformamide and in the presence of a catalytic amount of an aromatic amine hydrohalide or a quaternary or tertiary ammonium halide.

8. The process of claim 7 in which R$^1$ is located in the 5-, 6- or 8-position of the quinazoline ring system.

9. The process of claim 7 in which the N,N-dialkylformamide is dimethylformamide.

10. The process of claim 7 in which the aromatic amine hydrohalide or the quaternary or tertiary ammonium halide is a tetraalkylammonium chloride.

* * * * *